(12) United States Patent
Edwards (10) Patent No.: US 8,192,489 B2
(45) Date of Patent: Jun. 5, 2012

(54) IN SITU ADJUSTABLE OSSICULAR IMPLANT AND INSTRUMENT FOR IMPLANTING AND ADJUSTING AN ADJUSTABLE OSSICULAR IMPLANT

(75) Inventor: Kevin C. Edwards, Olive Branch, MS (US)

(73) Assignee: Gyrus Ent, L.L.C., Bartlett, TN (US)

( * ) Notice: Subject to any disclaimer, the term of this patent is extended or adjusted under 35 U.S.C. 154(b) by 82 days.

(21) Appl. No.: 12/879,653

(22) Filed: Sep. 10, 2010

(65) Prior Publication Data
US 2012/0065730 A1  Mar. 15, 2012

(51) Int. Cl.
*A61F 2/18* (2006.01)
(52) U.S. Cl. .......................................................... 623/10
(58) Field of Classification Search .................... 623/10; 600/25
See application file for complete search history.

(56) References Cited

U.S. PATENT DOCUMENTS

| | | | |
|---|---|---|---|
| 4,601,723 A | 7/1986 | McGrew | |
| 6,168,625 B1 | 1/2001 | Prescott | |
| 6,432,139 B1 | 8/2002 | Elies et al. | |
| 6,892,466 B2 | 5/2005 | Kurz et al. | |
| 6,942,696 B1 * | 9/2005 | White et al. | 623/10 |
| 7,553,328 B2 | 6/2009 | Steinhardt et al. | |
| RE40,853 E | 7/2009 | White et al. | |
| 7,603,788 B2 | 10/2009 | Kurz et al. | |
| 2003/0097178 A1 | 5/2003 | Roberson et al. | |
| 2009/0149697 A1 | 6/2009 | Steinhardt et al. | |
| 2010/0010629 A1 | 1/2010 | Bhansali | |
| 2011/0046731 A1 * | 2/2011 | Wiens et al. | 623/10 |

FOREIGN PATENT DOCUMENTS
WO  WO 2009/155610 A2  12/2009

OTHER PUBLICATIONS

Sep. 28, 2011 PCT International Search Report issued in PCT/US2011/043378.
Sep. 28, 2011 PCT Written Opinion issued in PCT/US2011/043378.

* cited by examiner

*Primary Examiner* — David Isabella
*Assistant Examiner* — Randy Shay
(74) *Attorney, Agent, or Firm* — Oliff & Berridge, PLC (57) ABSTRACT

A system for adjusting an adjustable ossicular prosthesis including an ossicular implant and an adjusting device is provided. The ossicular implant includes a first fixation element, an elongated member extending from the first fixation element with a plurality of notches, a receiving member receiving a portion of the elongated member, and a resilient arm coupled to the elongated member. The resilient arm has a locked position fixing the receiving member relative to the elongated member and the length of the implant, and an unlocked position. The adjusting device includes first and second arms having first and second sets of jaws coupled thereto, the first and second sets of jaws configured to selectively engage the implant, the second set of jaws being configured to position the resilient arm in the unlocked position when engaging the receiving member of the implant, and an adjustment mechanism to adjust the length of the implant.

19 Claims, 9 Drawing Sheets

IN SITU ADJUSTABLE OSSICULAR IMPLANT AND INSTRUMENT FOR IMPLANTING AND ADJUSTING AN ADJUSTABLE OSSICULAR IMPLANT

This application is directed to an adjustable ossicular implant and to systems and methods for implanting and adjusting the adjustable ossicular implant using an adjusting device.

BACKGROUND

Ossicular implants may be used as ossicular replacements for patients whose hearing has been negatively affected due to loss of function of components in the natural ossicular chain (malleus, incus and stapes).

The natural ossicular chain transmits sound waves from an internal surface of the tympanic membrane (eardrum) through the middle ear to the inner ear. When the natural ossicular chain no longer functions properly, surgical intervention may remove one or more of the ossicles (or portions of ossicles) and to replace them with prosthetic implants.

In implanting an ossicular prosthesis, the functional length of the implant is important for the success of the surgery. The proper length of the implant ensures that the implant mates securely with the locations of the middle ear to which it connects.

Implant lengths vary based on patient anatomy. Conventionally, implant length may be derived using sizers of known lengths or adjustable measuring tools. Once an implant length is determined, a one-piece implant of a preset length may be selected. Alternatively, a surgeon may attempt to set an adjustable length implant to the desired length outside of the patient. Conventional devices employ a method of adjusting and setting the implant length where, for example, a male component is adjusted inside a female component by the surgeon via a measuring "block." An exterior portion of the female component is generally manually crimped to a specific, unchangeable length using a crimping instrument, effectively squeezing the female component around the male component to secure the single and unchangeable length of the implant. The sized implant is then placed inside the patient and mated at each end with the desired locations in the middle ear.

A shortfall in prior art systems described above is that implant length may be difficult to measure accurately using conventional methods. The implant length may also be difficult to replicate when setting the implant outside the patient. The implant length will often not precisely fit the patient in a manner optimally desired by a surgeon.

Conventional methods to address these shortfalls center around differing instruments and techniques to attempt to accurately size, adjust and set implants prior to insertion into the patient. As illustrated above, conventional methods are limited to irreversibly setting a length of an implant once by a method that involves plastically deforming the implant's components such that the set length cannot be reset or adjusted further after crimping. Additionally, setting the length of conventional implants is a less-than-delicate operation. As such, the conventional length setting process is not conducive to, for example, any in situ application.

SUMMARY

It would be advantageous in view of the above discussion to provide systems and methods for adjusting and readjusting the length of an ossicular implant. Specifically, it would be advantageous to provide systems and methods for repeated in situ adjustment of an ossicular implant using an adjusting device. Such an implant would allow the surgeon to adjust its length and later readjust the length as appropriate based on any number of factors.

An additional advantage is that adjustable implants are generally desired for their ability to reduce hospital inventory. The hospital would only need to stock 1 adjustable implant instead of 10 different implants, of different sizes.

Exemplary ossicular implants according to this disclosure are repeatably adjustable to various lengths. A system for repeatedly adjusting the length of the ossicular implant, and a method for adjusting the length of the repeatably adjustable ossicular implant using an adjusting device are also described.

In exemplary embodiments, an ossicular replacement prosthesis system is provided that comprises: comprising: (a) an ossicular implant comprising: a first fixation element configured to couple the implant to a first location in the middle ear; an elongated member extending from the first fixation element; a plurality of notches positioned along the length of the elongated member; a receiving member receiving at least a portion of the elongated member; a resilient arm extending from the receiving member and coupled to the elongated member, the resilient arm having a locked position and an unlocked position, wherein, in the locked position, the resilient arm engages a notch on the elongated member and prevents movement of the receiving member in a direction of the elongated member, and, in the unlocked position, the resilient arm is disengaged from all of the plurality of notches on the elongated member and allows movement of the receiving member relative to the elongated member in the elongated direction; and a second fixation element extending from the receiving member, the second fixation element configured to couple the implant to a second location in the middle ear; and (b) an ossicular implant adjusting device comprising: a first arm having a first set of jaws coupled to a second arm having a second set of jaws; the first set of jaws configured to selectively engage the elongated member of the implant, the second set of jaws configured to selectively engage the receiving member of the implant; wherein the second set of jaws is also configured to position the resilient arm in the unlocked position when the second set of jaws engages the receiving member of the implant; and an adjustment mechanism configured to adjust a length of the implant by adjusting a distance between the first and second arms and configured to move the elongated member relative to the receiving member when the resilient arm is in the unlocked position.

In exemplary embodiments, the second fixation element and the receiving member may be held together by a connecting device.

In exemplary embodiments, the connecting device may be at least one of a pin and a weld.

In exemplary embodiments, the resilient arm may be biased to the locked position. As such, the second set of jaws of the ossicular implant adjusting device may engage the resilient arm in a manner that works against the bias of the resilient arm to move the resilient arm to the unlocked position.

In exemplary embodiments, the resilient arm may be formed of at least one of nitinol and titanium.

In exemplary embodiments, the plurality of notches may be formed as annular grooves in the elongated member.

In exemplary embodiments, the ossicular implant may be configured to be repeatedly lengthened or shortened along a longitudinal axis of the implant when the resilient arm is in the unlocked position.

In exemplary embodiments, the resilient arm may include at least part of an annular ring formed at an end thereof, the at least part of the annular ring engaging the notch on the elongated member in the locked position.

In exemplary embodiments, the first arm and the second arm of the ossicular implant adjusting device may be bent near an end having the first set of jaws and the second set of jaws, respectively.

In exemplary embodiments, the first arm and the second arm may be formed of stainless steel.

In exemplary embodiments, the ossicular implant adjusting device may be bilaterally symmetric.

In exemplary embodiments, movement of the first set of jaws to engage the elongated member may be independent of movement of the first arm and the second arm to adjust the distance between the first arm and the second arm.

In exemplary embodiments, the first arm may be formed from two parallel arms, the first set of jaws being formed near an end of the two parallel arms, a pair of handles being formed at an other end of the two parallel arms, and at least one of the two parallel arms including markings corresponding to a length of the implant, the second arm may be formed to at least partially receive the two parallel arms, the second set of jaws being formed near an end of the second arm, and the first arm and second arm may be configured to slide with respect to each other to adjust the length of the implant when the resilient arm is in the unlocked position.

In exemplary embodiments, the adjustment mechanism of the ossicular implant adjusting device may be a threaded wheel that is rotatable to control the relative separation of the first and second arms, thereby precisely setting the length of the ossicular implant.

In exemplary embodiments, the first and second sets of jaws may be configured to independently engage and release the ossicular implant.

In exemplary embodiments, a method for adjusting an ossicular implant using an adjusting device is provided, the method comprising: engaging the ossicular implant with a first set of jaws of an ossicular implant adjusting device (such as that described above); engaging the ossicular implant with a second set of jaws, the engaging with the second set of jaws including positioning a resilient arm of the ossicular implant in an unlocked position; adjusting, with an adjustment mechanism of the adjusting device, the length of the ossicular implant by adjusting the distance between the first and second arms; and releasing the ossicular implant with the first set of jaws and the second set of jaws, the releasing with the second set of jaws causing the resilient arm to be positioned in a locked position to fix the length of the ossicular implant, wherein the length adjustment of the ossicular implant is repeatable.

In exemplary embodiments, the length of the implant may be adjusted outside or inside a patient's ear.

In exemplary embodiments, the length of the implant may be adjusted to a predetermined length based on a marking on the adjusting device.

These and other features and advantages of the disclosed systems and methods are described in, or apparent from, the following detailed description of various exemplary embodiments.

BRIEF DESCRIPTION OF THE DRAWINGS

Various exemplary embodiments are described, in detail, with reference to the following figures, wherein elements having the same reference numeral designations represent like elements throughout, and in which.

DETAILED DESCRIPTION OF EMBODIMENTS

The following embodiments illustrate examples of systems and methods for adjusting an ossicular implant using an adjusting device. The following description of various exemplary embodiments may refer to specific arrangements of elements illustrated in the embodiments. However, it should be appreciated that, although the systems and methods according to this disclosure may be particularly adapted to the illustrated embodiments, the depictions and/or descriptions included in this disclosure are not intended to be limited to any specific configuration with regard to the adjustable ossicular implant, or the adjusting device.

It should be noted that, as used in this disclosure, the term ossicular implant refers to either or both total ossicular prostheses and partial ossicular prostheses.

Figure 1:
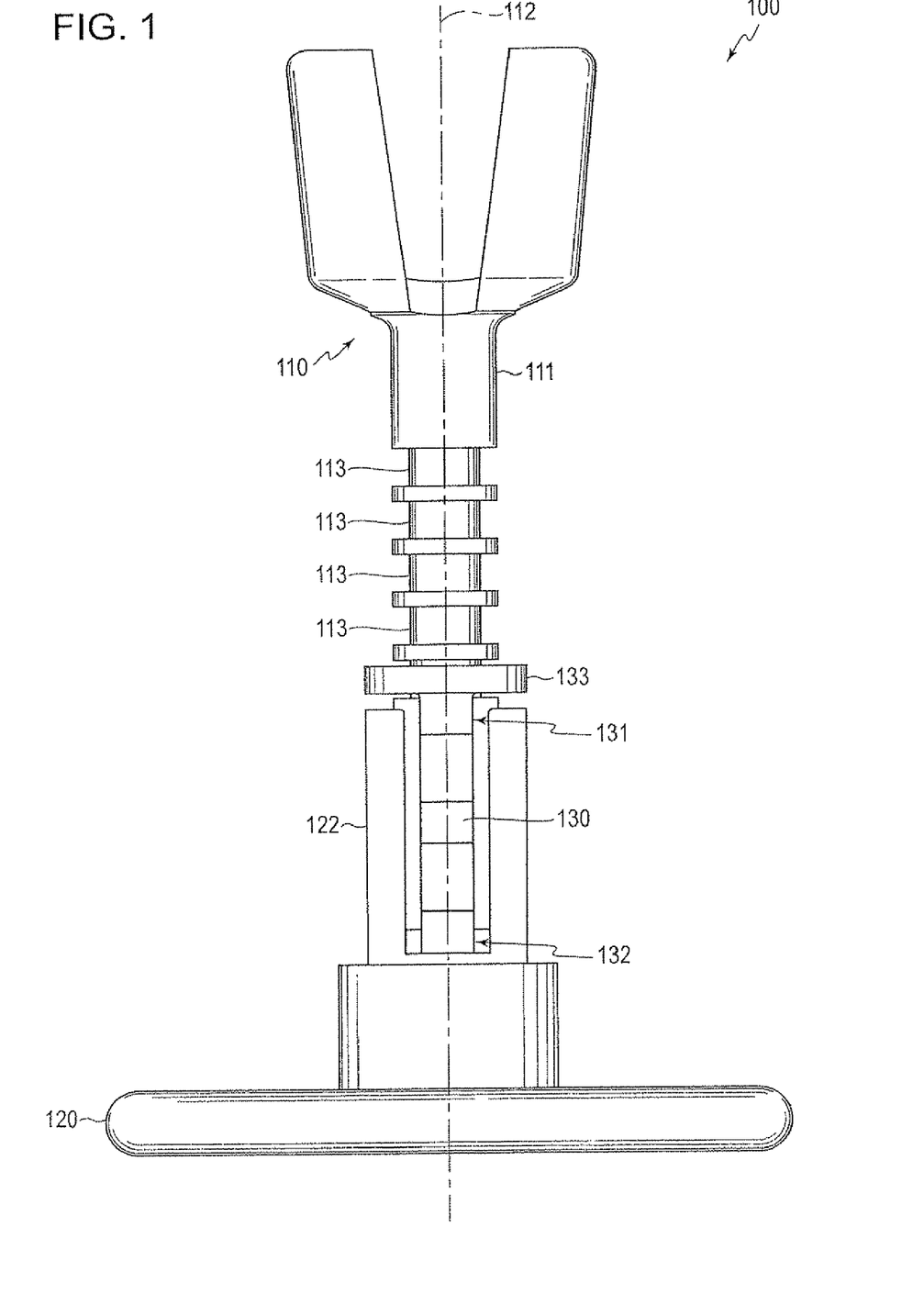
FIG. 1 illustrates an elevation view of a first exemplary embodiment of an ossicular implant according to the systems and methods of this disclosure.

Referring to FIG. 1, there is shown an elevation view of an exemplary embodiment of an ossicular implant 100. The ossicular implant 100 includes a first fixation element 110 configured to couple the implant 100 to a first location in the middle ear (not shown). For example, the first fixation element 110 may be configured to couple the implant 100 to an ossicle of a human ear. The first fixation element 110 includes an elongated member 111 along a longitudinal axis 112 of the ossicular implant 100. A plurality of notches 113 are arranged along the elongated member 111. The plurality of notches 113 may be formed, for example, as regularly spaced notches along the length of the elongated member 111. The plurality of notches 113 may also be formed as annular grooves in the elongated member 111.

The ossicular implant 100 may also include a receiving member 122 for receiving at least a portion of the elongated member 111.

The ossicular implant 100 may also include a resilient arm 130 extending from the receiving member 122, with a first end 131 and a second end 132. The resilient arm 130 may include an engaging element 133 toward the first end 131 of the resilient arm 130. The second end 132 of the resilient arm 130 may be connected to the receiving member 122. The engaging element 133 of the resilient arm 130 is, in use, repeatably movable between an unlocked position (illustrated, for example, in FIG. 2) and a locked position (illustrated, for example, in FIG. 3).

The ossicular implant 100 also may include a second fixation element 120 configured to couple the ossicular implant 100 to a second location in the middle ear (not shown). For example, the second fixation element 120 may be configured to couple the implant 100 with the tympanic membrane or an ossicle of the human ear. The second fixation element 120 may extend from the receiving member 122.

In the locked position, the engaging element 133 of the resilient arm 130 may engage at least one of the plurality of notches 113 to fix the elongated member 111 of the first fixation element 110 relative to the receiving member 122. In this manner, the length of the ossicular implant 100 may be fixed. In the unlocked position, the engaging element 133 of the resilient arm 130 may be disengaged from all of the notches 113. In this manner, movement of the elongated member 111 of the first fixation element 110 relative to the receiving member 122 may be facilitated, for example, along the longitudinal axis 112 of the ossicular implant 100 to adjust the length of the ossicular implant 100.

The resilient arm 130 is configured to be repeatedly moved between the locked position and the unlocked position, allowing repeated adjustment of the length of the implant 100 without permanently deforming any part of the implant 100. The resilient arm 130 is moved from the locked to the unlocked position by applying a force to the resilient arm 130. The force on the resilient arm 130 disengages the resilient arm 130 from the grooves or notches 113. While the resilient arm 130 is disengaged from the notches 113, the elongated member 111 may be moved relative to the receiving member 122, thereby adjusting the length of the implant 100. When the desired implant length is achieved, the force on resilient arm 130 is released and the resilient arm 130 returns to the locked position. The engaging element 133 of the resilient arm 130 may engage any one of the notches or grooves 113 in the locked position.

The second fixation element 120 of the ossicular implant 100 and the receiving member 122 may be formed as a single component or one-piece, or may be formed as separate components. If the second fixation element 120 and the receiving member 122 are formed as separate components, the resilient arm 130 may be connected to either the receiving member 122 or the second fixation element 120.

Figure 2:
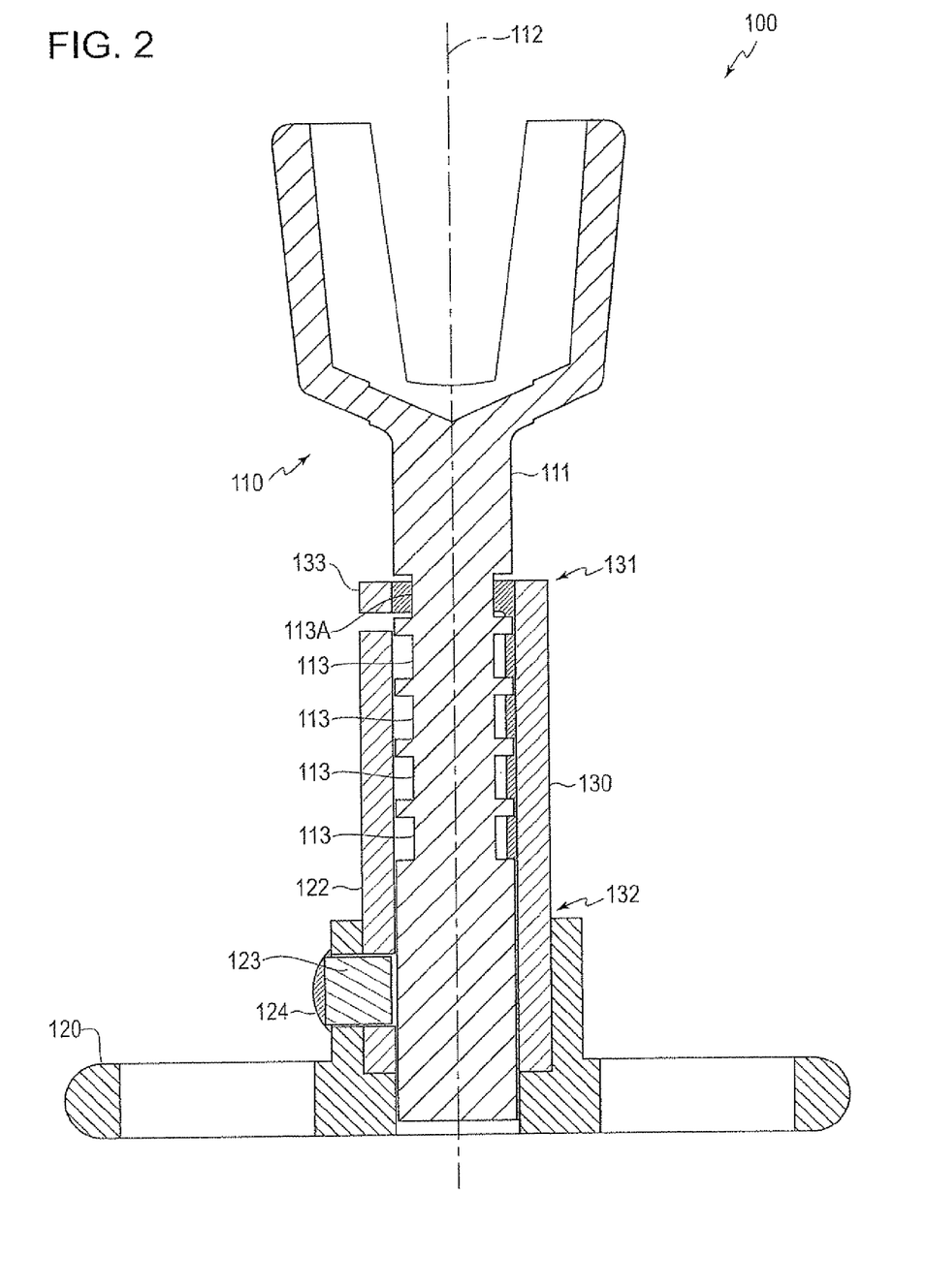
FIG. 2 illustrates an elevation view of a cross-section of the ossicular implant of FIG. 1.

Referring to FIG. 2, the second fixation element 120 may be held together with the receiving member 122 by a connecting device, such as a pin 123 or a weld 124.

FIG. 2 illustrates the ossicular implant 100 in a shortened and unlocked state. That is, the engaging element 133 of the resilient arm 130 is aligned with a last notch 113A of the plurality of notches 113. Additionally, FIG. 2 illustrates the resilient arm 130 in the unlocked position. That is, the engaging element 133 of the resilient arm 130 is spaced from, and not engaged with, any of the plurality of notches 113.

In the unlocked position illustrated in FIG. 2, the elongated member 111 is movable relative to the receiving member 122. In this position, the length of the ossicular implant 100 may be freely adjusted. A benefit of this configuration is the ability to repeatedly readjust the length of the ossicular implant.

Figure 3:
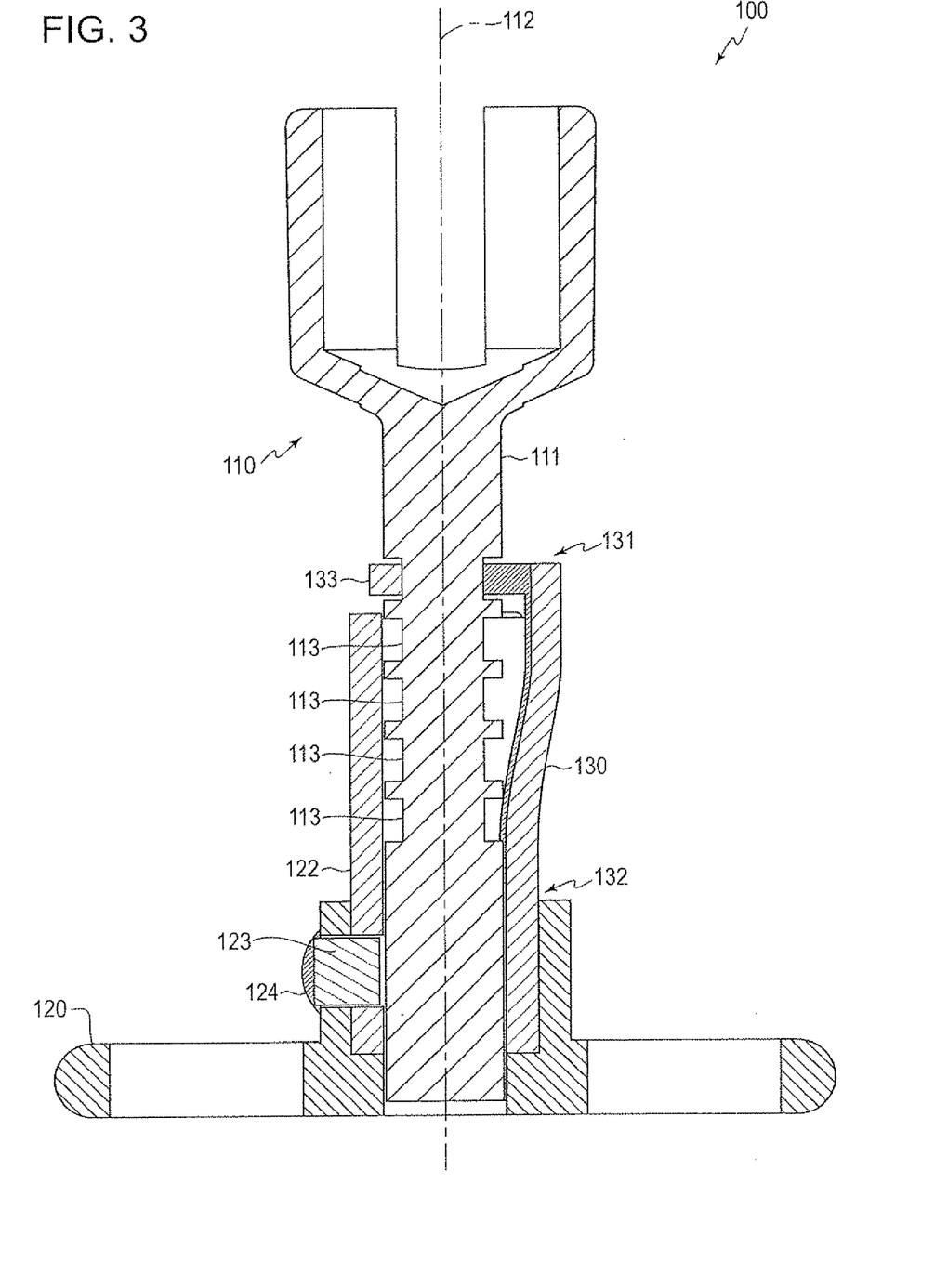
FIG. 3 illustrates an elevation view of the cross-section of the ossicular implant of FIG. 2, with a resilient arm in a locked position.

FIG. 3 illustrates the ossicular implant 100 with the resilient arm in the locked position. That is, the engaging element 133 of the resilient arm 130 is positioned in one of the notches 113. In this manner, the elongated member 111 of the first fixation element 110 may be fixed relative to the receiving member 122 and the second fixation element 120, thereby fix the length of the ossicular implant 100 at a specific length.

The resilient arm 130 may be formed of an appropriately resilient material. For example, the resilient arm 130 may be formed of nitinol, which is especially useful for its excellent superelastic and shape memory properties. The resilient arm 130 may also be formed of titanium, or other resilient metals or composite materials. The resilient arm 130 and the engaging element 133 may be biased to the locked position. Biasing the resilient arm 130 and the engaging element 133 in the locked position allows the length of the ossicular implant 100 to be fixed when the resilient arm 130 of the ossicular implant 100 is released by an ossicular implant adjusting device. That is, biasing the resilient arm 130 and the engaging element 133 in the locked position fixes the length of the ossicular implant 100 unless and until the resilient arm 130 is actively moved to the unlocked position.

The engaging element 133 of the resilient arm 130 may be formed in any suitable shape that allows the engaging element 133 to engage and disengage with at least one of the plurality of notches 113. For example, the engaging element 133 of the resilient arm 130 may be formed as an annular ring. Alternatively, the engaging element 133 may be formed as only a part of an annular ring.

Figure 4:
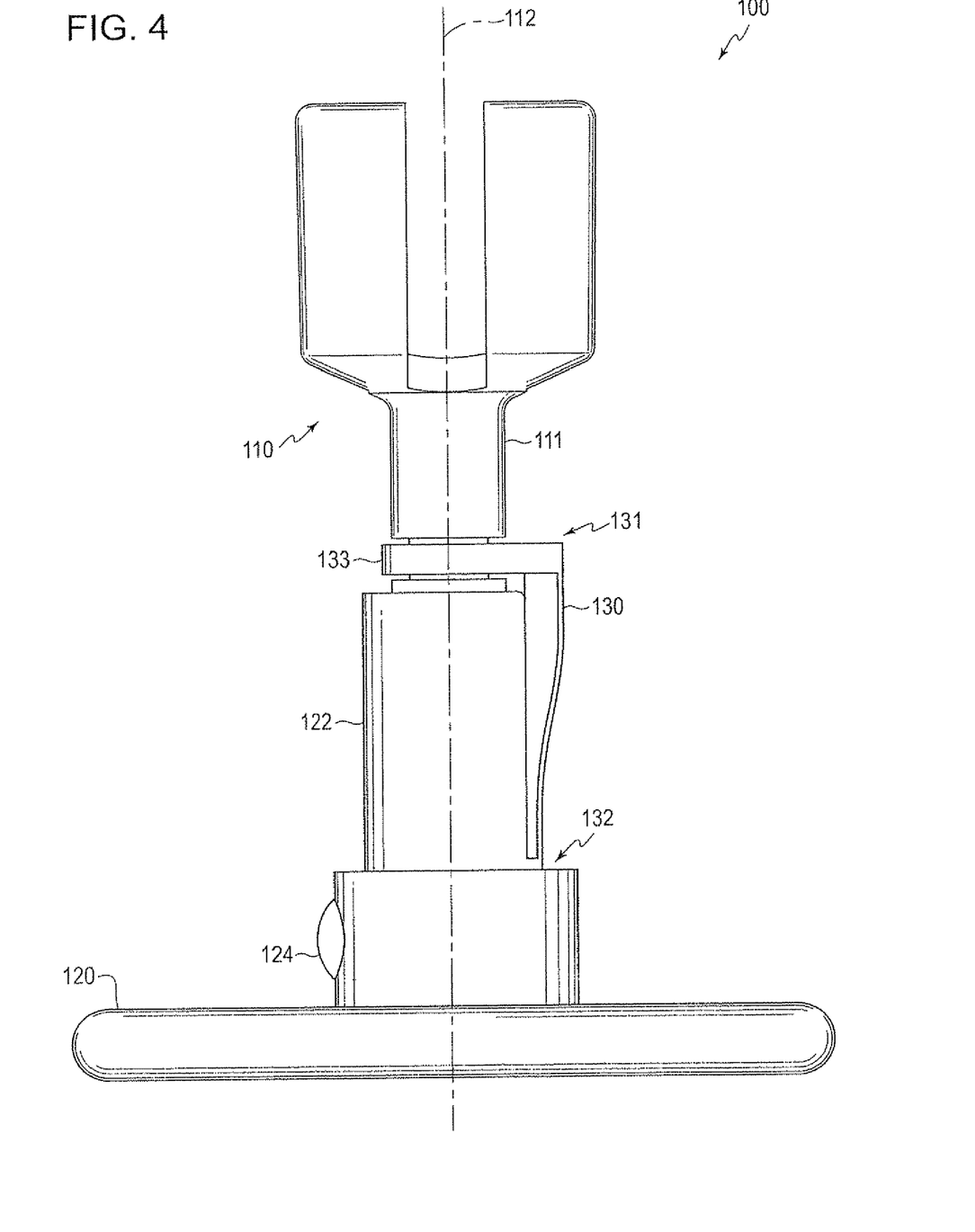
FIG. 4 illustrates an elevation view of the ossicular implant of FIG. 3.

FIG. 4 illustrates the ossicular implant 100 with the resilient arm in the locked position, similar to FIG. 3. That is, the engaging element 133 of the resilient arm 130 is positioned in one of the notches 113. In this manner, the elongated member 111 is fixed relative to the receiving member 122, and the implant 100 is fixed at a specific length. This length may be adjusted again by disengaging the engaging element 133 of the resilient arm 130 from the groove or notch 113 and moving the engaging element 133 to be positioned within another groove or notch 113.

Figure 5:
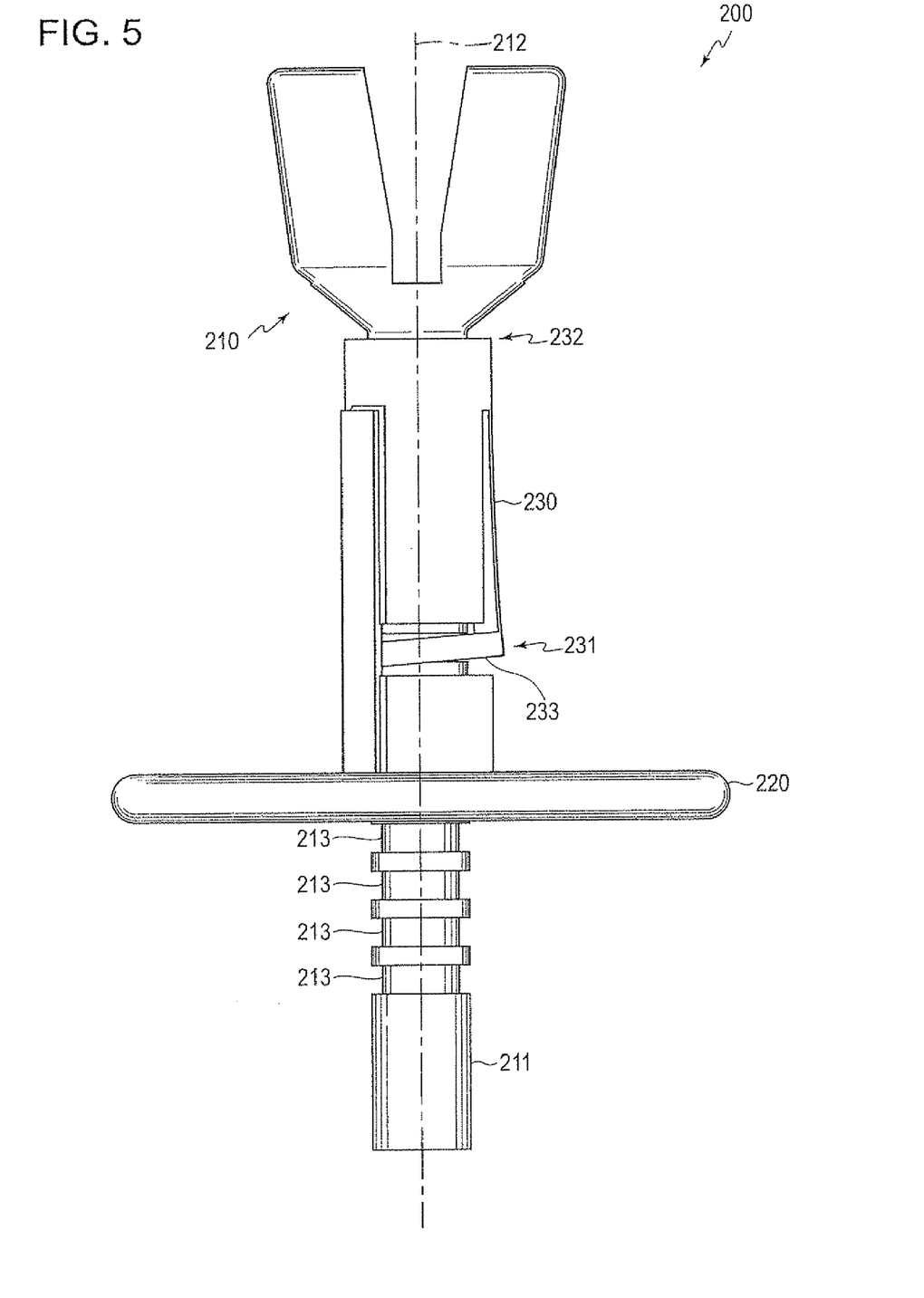
FIG. 5 illustrates an elevation view of a second exemplary embodiment of an ossicular implant.

FIG. 5 illustrates a second exemplary embodiment of an ossicular implant 200 having a first fixation element 210 and a second fixation element 220. A plurality of notches 213 are formed on an elongated member 211 of the first fixation element 210. The elongated member 211 is elongated along a longitudinal axis 212 of the ossicular implant 200.

In the ossicular implant 200 illustrated in FIG. 5, the first end 231 of the resilient arm 230 and the second end 232 of the resilient arm 230 may be reversed in position along the longitudinal axis 212, as compared to the exemplary embodiment illustrated in FIGS. 1-4. The reversal of the resilient arm 230 position may make the implant easier to put together and easier to manufacture. In addition, the new position of the resilient arm 230 may also make it easier for a surgeon to apply force, because the force applied by the tool may be closer to the center of the resilient arm 230.

Figure 6A:
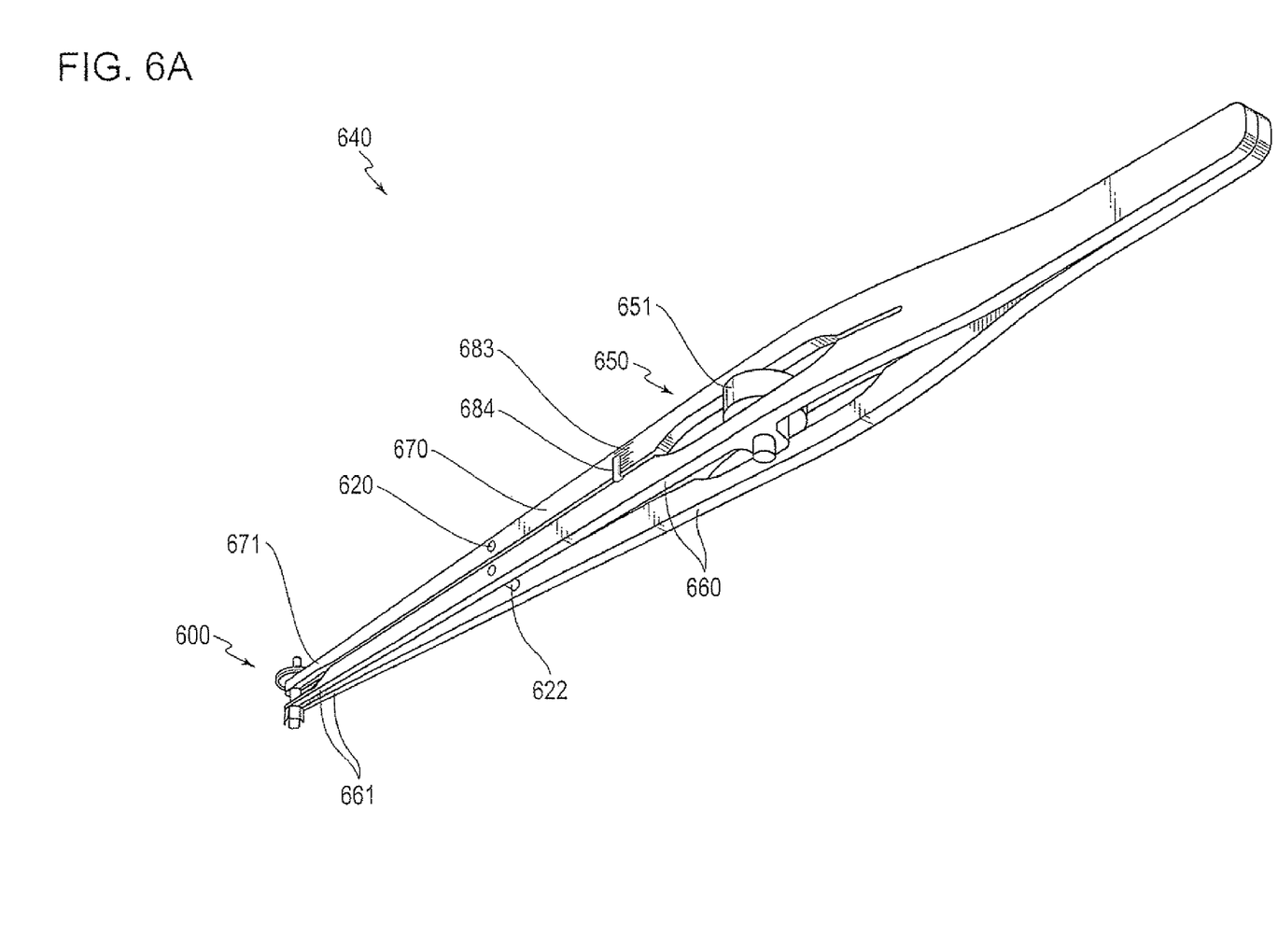
FIG. 6A illustrates a perspective view of an ossicular implant adjusting device according to the systems and methods of this disclosure.
Figure 7A:
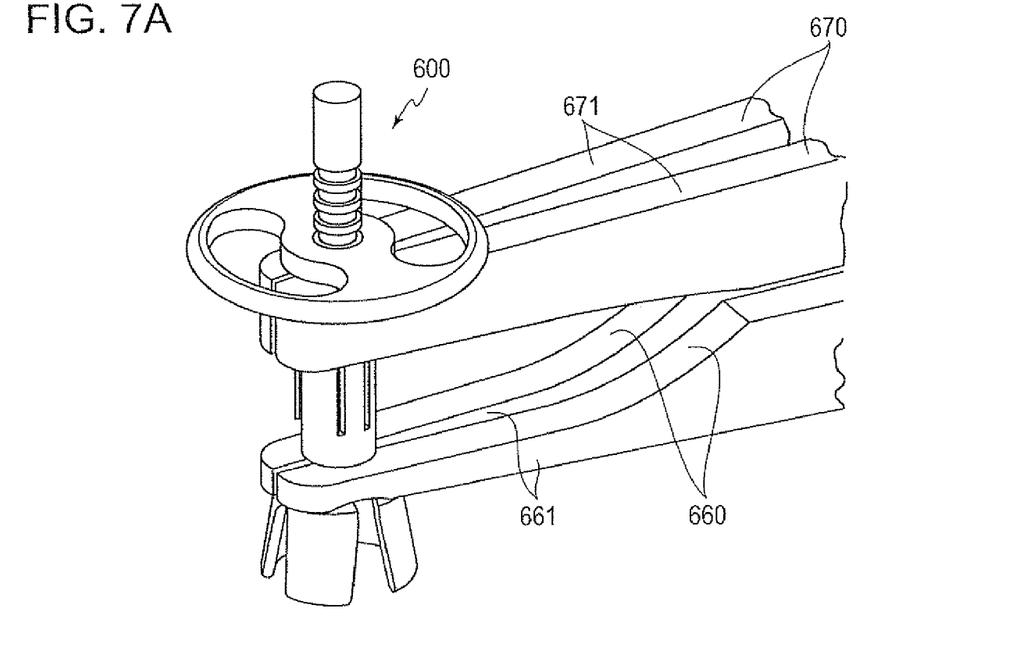
FIG. 7A illustrates an enlarged perspective view of the jaws of the ossicular implant adjusting device of FIG. 6A, and is shown grasping an ossicular implant according to the systems and methods of this disclosure.

Referring to FIGS. 6A and 7A, an exemplary ossicular replacement prosthesis system is shown. An ossicular implant adjusting device 640 includes a first arm 660 having a first set of jaws 661 coupled to a second arm 670 having a second set of jaws 671. The first set of jaws 661 are configured to selectively engage an elongated member of an ossicular implant 600. The second set of jaws 671 are configured to selectively engage a receiving member of the ossicular implant 600. The second set of jaws 671 are also configured to move a resilient arm of the ossicular implant 600 to the unlocked position by applying a force to a portion of the resilient arm 130 when the second set of jaws 671 engages the receiving member of the ossicular implant 600. The ossicular implant adjusting device 640 includes an adjustment mechanism 650 configured to adjust a length of the implant 600 by adjusting a distance between the first arm 660 and the second arm 670 when the resilient arm of the implant 600 is in the unlocked position.

In order to facilitate implanting an ossicular prosthesis due to size and space limitations, the first arm 660 and the second arm 670 may be bent near an end of the adjusting device 640 having the first set of jaws 661 and the second set of jaws 671.

The first arm 660 and the second arm 670 may be formed of any suitable material. For example, the first arm 660 and the second arm 670 may be formed of stainless steel, but the first arm 660 and the second arm 670 need not be formed of any specific material.

Figure 7B:
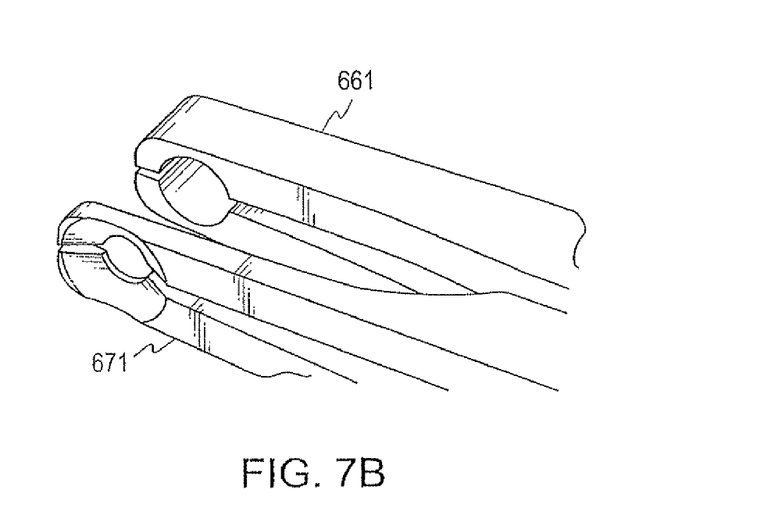
FIG. 7B illustrates an enlarged perspective view of the jaws of the ossicular implant adjusting device of FIG. 6A.

Referring to FIG. 7B, an enlarged view of the jaws 661 and 671 is shown without the implant. Each arm of the jaw may include a recessed portion for holding the adjustable implant while the tool adjusts the implant length. The arms of the jaws 661 are coupled together through a pin 620 and the arms of the jaws 671 are coupled together through a pin 622. The pins 620 and 622, shown in FIG. 6A, couple the arms of the jaw together so that when the adjustment mechanism 650 is used, the arms of the jaws 661 move together and the arms of the jaws 671 move together.

Additionally, the adjusting device 640 may be formed to be bilaterally symmetric. That is, one side of the adjusting device 640 may be formed as a mirror image of the other side.

Movement of the first set of jaws 661 to engage the elongated member of the ossicular implant 600 may be independent of movement of the second set of jaws 671 to engage the receiving member of the implant 600. Alternatively, the first set of jaws 661 and the second set of jaws 671 may be configured to engage and release the implant 600 at the same time.

Engagement of the first set of jaws 661 and the second set of jaws 671 may be independent of movement of the first arm 660 and the second arm 670 to adjust the distance between the first arm 660 and the second arm 670.

Figure 6B:
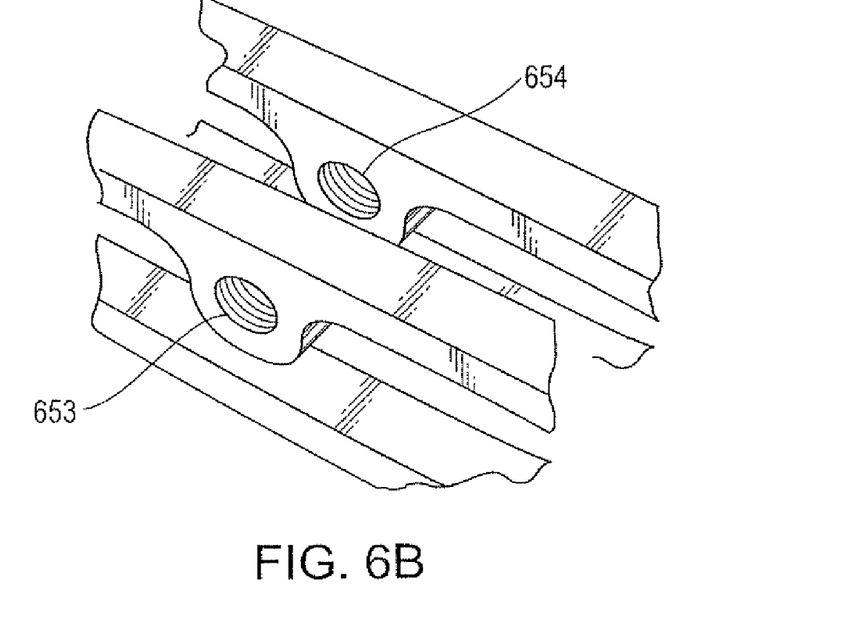
FIG. 6B illustrates an enlarged view of a portion of an adjustment mechanism of the device shown in FIG. 6A.
Figure 6C:
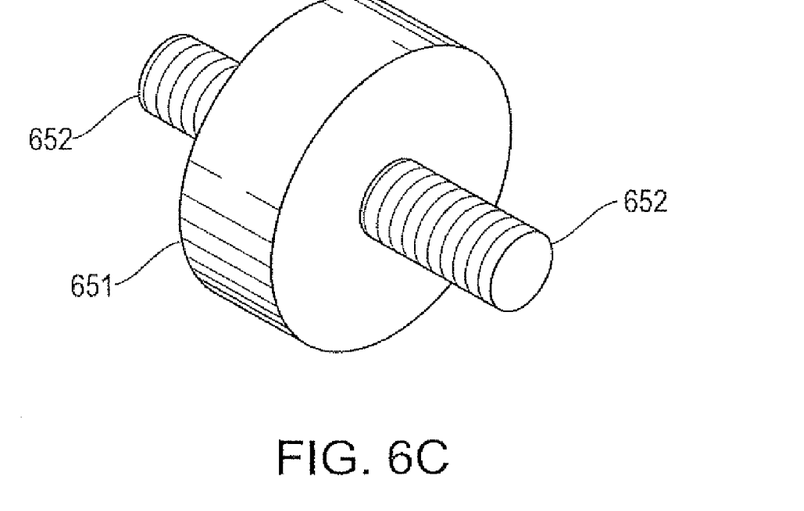
FIG. 6C illustrates an enlarged view of another portion of the adjustment mechanism of the device shown in FIG. 6A.

Referring to FIGS. 6B and 6C, an exploded view of an adjustment mechanism is shown. The adjustment mechanism 650 may include a threaded wheel 651. By turning the threaded wheel 651, the relative separation between the first arm 660, and the second arm 670 may be controlled during an initial process of adjusting a length of the ossicular implant, or during any one of a plurality of available readjustments of the length of the ossicular implant. The threaded wheel 651 may be coupled to a post 652. At each end of the post 652 are male threads having opposite threads (e.g. one end will have a right hand thread and the other one will have a left hand thread). Each threaded end may be positioned within a mating thread opening 653, 654 located on the arms 660 and 670. As the threaded wheel 651 is turned in a first direction, the jaws 661 and 671 will move in a direction relative to each other. When the threaded wheel is turned in the opposite direction, the jaws 661 and 671 will move in the opposite direction as to when the wheel 651 was first turned. The relative separation and corresponding implant length may be judged using graduated markings 683 on one of the arms 660 and 670 of the adjusting device 640, in connection with a protrusion 684 on the other of the arms 660 and 670. As the adjustment mechanism 650 is adjusting the distance between the first arm 660 and the second arm 670, the relative distance may be monitored by the position of the protrusion 684 with respect to the graduated markings 683. The relative distance between the first arm 660 and second arm 670 may correlate to the adjusted length of the implant 100, allowing the surgeon to set the length of the adjustable implant 100. Other adjusting mechanisms may be used to control the relative separation between the first arm 660 and the second arm 670. For example, a sleeve with gradations or other markings may be used to separate the first set arm and the second set arm by sliding the sleeve along the longitudinal direction of the adjusting device.

To use the adjusting device 640, a surgeon may squeeze the members of the first arm 660, thus closing the first set of jaws 661 around the elongated member of the ossicular implant 600. The surgeon may also squeeze the members of the second arm 670, thus closing the second set of jaws 671 around the receiving member in a manner that the resilient arm of the ossicular implant 600 is moved to an unlocked position. Squeezing the members of the second arm 670 and closing the second set of jaws 671 around the receiving member and resilient arm of the ossicular implant 600 disengages the resilient arm from the notches on the elongated member by providing a pressure or a force on the resilient arm of the implant and places the resilient arm in the unlocked position. The surgeon may then turn the threaded wheel 651 to adjust the length of the ossicular implant 600 by adjusting the separation of the first arm 660 relative to the second arm 670. The movement of the first arm 660 relative to the second arm 670, when the adjusting device 640 is coupled to the adjustable implant 600, also adjusts the length of the implant 600. Once a desired length of the implant 600 is achieved, as measured, for example, using the graduated markings 683 in connection with the protrusion 684, the surgeon relieves pressure on the second arm 670 to allow the resilient arm to return into a notch of the elongated member in the locked position, thus fixing the length of the ossicular implant 600. The surgeon may relieve the pressure on the resilient arm by uncoupling the adjusting device 640 from the implant 600. Adjustment of the length of the implant 600 may be repeated as appropriate. The adjustment or readjustment of the implant may be performed inside or outside the patient.

Figure 8:
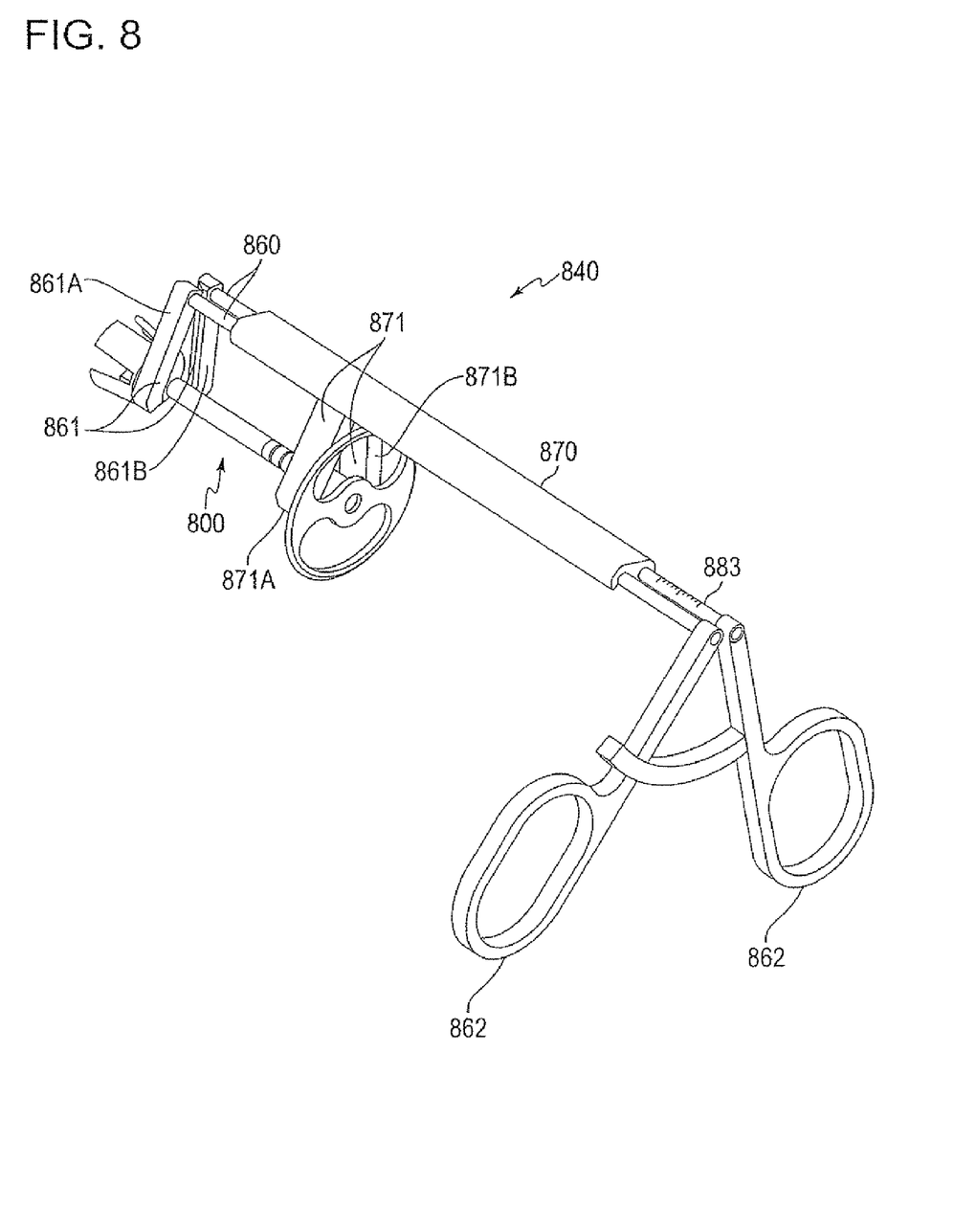
FIG. 8 illustrates a perspective view of an ossicular implant adjusting device and an ossicular implant according to the systems and methods of this disclosure.

Referring to FIG. 8, a second exemplary embodiment of an ossicular implant adjusting device 840 is shown. The ossicular implant adjusting device 840 includes a first arm 860 formed from two parallel arms. A first set of jaws 861 is formed on the two parallel arms near an end of the first arm 860. Each of the jaws 861 may include a gripping surface, similar to that shown in FIG. 6B, so that the implant may be securely engaged by the jaws when the adjustment tool is in use. A pair of handles 862 are formed on the two parallel arms near the other end of the first arm 860. At least one of the two parallel arms may include markings 883 corresponding to a length of an ossicular implant 800.

A second arm 870 is formed as a sleeve to at least partially receive the two parallel arms of the first arm 860. A second set of jaws 871 is formed near an end of the second arm 870. The first arm 860 and the second arm 870 are configured to be slidable with respect to each other to adjust the length of the ossicular implant 800 when the a resilient member of the ossicular implant 800 is moved to an unlocked position.

The first set of jaws 861 may comprise jaws 861A and 861B, and the second set of jaws 871 may comprise jaws 871A and 871B. In the embodiment illustrated in FIG. 8, jaws 861A and 871A move as one, and jaws 861B and 871B also move as one. Alternatively, jaws 861A and 871A may be configured to move independently, and jaws 861B and 871B may also be configured to move independently.

To use the adjusting device 840, a surgeon may operate the handles 862 like scissors to close the first set of jaws 861 and the second set of jaws 871 around the ossicular implant 800. The first set of jaws 861 and second set of jaws 871 are closed by, for example, rotating the two parallel members of the first arm 860 by adjusting the handle. When the first set of jaws 861 and second set of jaws 871 are closed around the ossicular implant 800, the second set of jaws 871 moves the resilient arm of the ossicular implant 800 to the unlocked position. The surgeon may then adjust the length of the ossicular implant 800 by grasping and sliding the second arm 870 relative to the first arm 860. The second arm 870 moves the jaws 871 relative to the jaws 861. The surgeon may judge the length of the implant 800 using the markings 883. The end of the second arm 870 may be used to determine the current length of the implant with respect to the markings 883. Once the desired length of the implant 800 is achieved, the surgeon may release the first set of jaws 861 and the second set of jaws 871 by operating the handles 862, and allowing the resilient arm of the ossicular implant 800 to return to the locked position, to which it is biased, to fix the length of the ossicular implant 800. Adjustment of the length of the implant 800 may be repeated as appropriate. The adjustment or readjustment of the implant may be performed inside or outside the patient.

It will be appreciated that various of the above-disclosed and other features and functions, or alternatives thereof, may be desirably combined into other different systems or applications. Also, various presently unforeseen or unanticipated alternatives, modifications, variations or improvements may be subsequently made by those skilled in the art, and are also intended to be encompassed by the following claims.

What is claimed is:

1. An ossicular replacement prosthesis system comprising:
   (a) an implant comprising:
      a first fixation element configured to couple the implant to a first location in the middle ear;
      an elongated member extending from the first fixation element;
      a plurality of notches positioned along the length of the elongated member;
      a receiving member receiving at least a portion of the elongated member;
      a resilient arm extending from the receiving member and coupled to the elongated member, the resilient arm having a locked position and an unlocked position, wherein, in the locked position, the resilient arm engages a notch on the elongated member and prevents movement of the receiving member relative to the elongated member, and, in the unlocked position, the resilient arm is disengaged from all of the plurality of notches on the elongated member and allows movement of the receiving member relative to the elongated member; and
      a second fixation element extending from the receiving member, the second fixation element configured to couple the implant to a second location in the middle ear; and
   (b) an implant adjusting device comprising:
      a first arm having a first set of jaws coupled to a second arm having a second set of jaws;
      the first set of jaws configured to selectively engage the elongated member of the implant, the second set of jaws configured to selectively engage the receiving member of the implant;
      wherein the second set of jaws is also configured to position the resilient arm in the unlocked position when the second set of jaws engages the receiving member of the implant; and
      an adjustment mechanism configured to adjust a length of the implant by adjusting a distance between the first and second arms and configured to move the elongated member relative to the receiving member when the resilient arm is in the unlocked position,
   wherein the length of the implant is repeatedly adjustable.

2. The system according to claim 1, wherein the second fixation element and the receiving member are held together by a connecting device.

3. The system according to claim 2, wherein the connecting device is at least one of a pin and a weld.

4. The system according to claim 1, wherein the resilient arm is biased to the locked position.

5. The system according to claim 1, wherein the resilient arm is formed of at least one of nitinol and titanium.

6. The system according to claim 1, wherein the plurality of notches are formed as annular grooves in the elongated member.

7. The system according to claim 1, wherein the resilient arm includes at least part of an annular ring formed at an end thereof, the at least part of the annular ring engaging the notch on the elongated member in the locked position.

8. The system according to claim 1, wherein the first arm and the second arm are bent near an end having the first set of jaws and the second set of jaws, respectively.

9. The system according to claim 1, wherein the first arm and the second arm are formed of stainless steel.

10. The system according to claim 1, wherein the implant adjusting device is bilaterally symmetric.

11. The system according to claim 1, wherein movement of the first set of jaws to engage the elongated member is independent of movement of the first arm and the second arm to adjust the distance between the first arm and the second arm.

12. The system according to claim 1, wherein
   the first arm is formed from two parallel arms, the first set of jaws being formed near an end of the two parallel arms, a pair of handles being formed at an other end of the two parallel arms, and at least one of the two parallel arms including markings corresponding to a length of the implant,
   the second arm is formed to at least partially receive the two parallel arms, the second set of jaws being formed near an end of the second arm, and
   the first arm and second arm are configured to slide with respect to each other to adjust the length of the implant when the resilient arm is in the unlocked position.

13. The system according to claim 1, wherein the adjustment mechanism is a threaded wheel that is rotatable to control the relative separation of the first and second arms.

14. The system according to claim 1, wherein the first and second sets of jaws are configured to independently engage and release the implant.

15. A method for adjusting an ossicular implant using an adjusting device, the ossicular implant comprising:
   a first fixation element configured to couple the ossicular implant to a first location in the middle ear;
   an elongated member extending from the first fixation element;
   a plurality of notches positioned along the length of the elongated member;
   a receiving member receiving at least a portion of the elongated member;
   a resilient arm extending from the receiving member and coupled to the elongated member, the resilient arm having a locked position and an unlocked position, wherein, in the locked position, the resilient arm engages a notch on the elongated member and prevents movement of the receiving member relative to the elongated member, and, in the unlocked position, the resilient arm is disengaged from all of the plurality of notches on the elongated member and allows movement of the receiving member relative to the elongated member; and a second fixation element extending from the receiving member, the second fixation element configured to couple the implant to a second location in the middle ear;

the adjusting device comprising:

a first arm having a first set of jaws coupled to a second arm having a second set of jaws;

the first set of jaws configured to selectively engage the elongated member of the ossicular implant, the second set of jaws configured to selectively engage the receiving member of the ossicular implant;

wherein the second set of jaws is also configured to position the resilient arm in the unlocked position when the second set of jaws engages the receiving member of the ossicular implant; and an adjustment mechanism configured to adjust a length of the ossicular implant by adjusting a distance between the first and second arms and configured to move the elongated member relative to the receiving member when the resilient arm is in the unlocked position;

the method comprising:

engaging the ossicular implant with the first set of jaws;

engaging the ossicular implant with the second set of jaws, the engaging with the second set of jaws positioning the resilient arm in the unlocked position;

adjusting length of the ossicular implant by adjusting the distance between the first and second arms with the adjustment mechanism of the adjusting device; and releasing the ossicular implant with the first set of jaws and the second set of jaws, the releasing with the second set of jaws positioning the resilient arm in the locked position to fix the length of the ossicular implant, wherein the length of the implant is repeatedly adjustable.

16. The method according to claim 15, wherein the length of the ossicular implant is adjusted outside a patient's ear.

17. The method according to claim 15, wherein the length of the ossicular implant is adjusted inside a patient's ear.

18. The method according to claim 15, wherein the length of the ossicular implant is adjusted a plurality of times.

19. The method according to claim 15, wherein the length of the implant is adjusted and fixed to a predetermined length based on a marking on the adjusting device.

* * * * *